United States Patent [19]

Antelman

[11] Patent Number: 5,336,499
[45] Date of Patent: Aug. 9, 1994

[54] MOLECULAR CRYSTAL DEVICE FOR PHARMACEUTICALS

[75] Inventor: Marvin S. Antelman, Rehovot, Israel

[73] Assignee: Antelman Technologies, Ltd., Providence, R.I.

[21] Appl. No.: 971,933

[22] Filed: Nov. 5, 1992

Related U.S. Application Data

[62] Division of Ser. No. 820,282, Jan. 10, 1992, abandoned.

[51] Int. Cl.$^5$ ............................................. A61K 7/00
[52] U.S. Cl. ..................................... 424/405; 424/618; 424/709; 514/495; 423/604; 210/759; 210/764; 422/19; 422/28
[58] Field of Search ................... 424/405, 618, 709; 423/604, DIG. 17; 210/764, 759; 422/28, 19; 514/495

[56] References Cited

U.S. PATENT DOCUMENTS

| | | | |
|---|---|---|---|
| 4,695,353 | 9/1987 | Jansen et al. | 423/604 |
| 4,717,562 | 1/1988 | Jansen et al. | 423/604 |
| 4,835,077 | 5/1989 | Megahed et al. | 423/604 |
| 5,017,295 | 5/1991 | Antelman | 424/618 |
| 5,073,382 | 12/1991 | Antelman | 424/601 |
| 5,078,902 | 1/1992 | Antelman | 424/601 |
| 5,089,248 | 2/1992 | Akhtar | 423/604 |
| 5,089,275 | 2/1992 | Antelman | 424/601 |

*Primary Examiner*—Thurman K. Page
*Assistant Examiner*—Amy Hulina
*Attorney, Agent, or Firm*—Salter & Michaelson

[57] ABSTRACT

A novel molecular scale device is described which is bactericidal, fungicidal, viricidal and algicidal. The anti-pathogenic properties of the device are attributed to electron activity indigenous to diamagnetic semiconducting crystals of tetrasilver tetroxide ($Ag_4O_4$) which contains two monovalent and two trivalent silver ions in each molecular crystal. When the crystals are activated with an oxidizing agent, they release electrons equivalent to $6.4 \times 10^{-19}$ watts per molecule which in effect electrocute pathogens. A multitude of these devices are effective at such low concentrations as 0.3 PPM used as preservatives in a variety of formulations ranging from cosmetics to pharmaceuticals. Indeed, they are intended as active ingredients for pharmaceuticals formulated to destroy such pathogens as Staphylococcus aureus, and epidermidis, the latter of which it completely destroys in a nutrient broth culture of about 1 million organisms at 0.6 PPM, or Candida albicans, the vaginal yeast infection at 2.5 PPM, and the AIDS virus at 18 PPM.

1 Claim, 1 Drawing Sheet

MOLECULAR CRYSTAL DEVICE FOR PHARMACEUTICALS

This is a division of application Ser. No. 07/820,282 filed Jan. 10, 1992 now abandoned.

BACKGROUND OF THE INVENTION

The present invention relates to the employment of molecular crystals as bactericidal, viricidal and algicidal devices, but more particularly to the molecular semiconductor crystal tetrasilver tetroxide $Ag_4O_4$ which has two trivalent and two monovalent silver atoms per molecule, and which through this structural configuration enables electronic activity on a molecular scale capable of killing algae and bacteria via the same mechanism as macroscale electron generators. The concept of molecular scale semiconductor devices for the storage of information has been the subject of much activity in recent years so that the concept of a molecular scale device performing such functions as storing information or acting as resistors, capacitors or photovoltaic devices is well accepted. The molecular device of this invention is a multivalent silver diamagnetic semiconductor. Now the bactericidal activity of soluble divalent silver (Ag II) complex bactericides is the subject of U.S. Pat. No. 5,017,285 of the present inventor. The inventor has also been granted U.S. Pat. Nos. 5,078,902, 5,073,382, 5,089,275, and 5,098,582, which all deal with Ag II bactericides but more particularly with (respectively) halides, alkaline pH, stabilized complexes and the divalent oxide. It is the last patent, i.e., U.S. Pat. No. 5,098,582, and its perfection that has led to my original concept of the molecular device of the present invention. Now said patent designated AgO as divalent silver oxide, the popular name of the compound. Indeed, the Merck Index (11th Edition) designates the oxide as silver(II) oxide (AGO) (entry 8469). However, it also states that it is actually a silver(I)-silver(III) oxide with a molecular weight of 123.88. Said oxide is actually on a molecular level $Ag_4O_4$ where one pair of silver ions in the molecule is trivalent and another pair is monovalent.

While the formula AgO accurately designates the silver:oxygen ratio, the molecular weight of the compound is actually 495.52. Further elucidation of the molecule's electromagnetic properties reveals that it is a diamagnetic semiconductor. The structure is electronically active because of the trivalent $sp^2$ electron configuration disparity of the electrons within the crystal.

Further testing of the unique oxide was continued on various types of bacteria, molds, yeasts and algae, beyond the water treatment applications claimed in my previous patents. The phenomenal efficacy of said oxide against pathogens while they were in constant contact with their nutrient source in contradistinction to its efficacy with these same organisms in water, where the pathogen is separated from a constant nutrient source, could only be accounted for by considering each molecule of oxide as a "device". This in turn has led to the final development of this invention, namely, a molecular device for killing viruses, fungi, algae and bacteria, which can be utilized as the active component of pharmaceuticals and as a preservative against said pathogens in pharmaceutical and other products.

OBJECTS OF THE INVENTION

The main object of this invention is to provide for a molecular scale device of a single tetrasilver tetroxide semiconductor crystal capable of killing viruses, bacteria, fungi and algae when operating in conjunction with other such devices.

Another object of the invention is to provide for a molecular device which can be utilized in pharmaceuticals formulated to destroy pathogens.

Still another object of the invention is as a preservative in pharmaceutical, cosmetic, and related chemical specialty products against said pathogens.

Other objects and features of the present invention will become apparent to those skilled in the art when the present invention is considered in view of the accompanying examples. It should, of course, be recognized that the accompanying examples illustrate preferred embodiments of the present invention and are not intended as a means of defining the limits and scope of the present invention.

SUMMARY OF THE INVENTION

This invention relates to a molecular scale device capable of destroying gram positive and gram negative bacteria as well as fungi, viruses and algae. Said molecular scale device consists of a single crystal of tetrasilver tetroxide. Several hundred thousand trillion of these devices may be employed in concert for their bactericidal, fungicidal, and algicidal properties and applied to industrial cooling towers, swimming pools, hot tubs, municipal water supplies and various pharmaceutical formulations.

The molecular crystals which are the subject of this invention are commercially available and can be prepared by reacting silver nitrate with sodium or potassium peroxydisulfate according to the following equation: $4AgNO_3 + 2Na_2S_2O_8 + 8NaOH = Ag_4O_4 + 4Na_2SO_4 + 4NaNO_3 + 4H_2O$ The oxide lattice represented by the formula $Ag_4O_4$ is depicted in the Drawing FIG. 1. It is a semiconducting electron active diamagnetic crystal containing two monovalent and two trivalent silver ions in combination with four oxygen atoms. The distance between the Ag(III)—O Ag(I)O units equals 2.1 A. Ag(III)—Ag(III)=Ag(I)—Ag(I)=3.28A and Ag(I)—Ag(III)=3.39 A. Each trivalent silver ion is coordinated via $dsp^2$ electron bonds to 4 oxygen atoms. The depiction of this lattice is based on several literature references relating to crystallographic studies. Exemplary of this literature are J. A. McMillan's studies appearing in *Inorganic Chemistry* 13,28 (1960); *Nature* vol. 195 No. 4841 (1962), and *Chemical Reviews* 1962, 62,65. Alvin J. Salkind elucidated studies involving neutron diffraction with his coworkers (*J. Ricerca Sci.* 30, 1034 1960) proving the Ag(III)/Ag(I) nature of this molecule and states in his classic entitled *Alkaline Storage Batteries* (Wiley 1969), coauthored with S. Uno Falk, that the formula is depicted by $Ag_4O_4$ (page 156).

That same year a scientific communication appeared in *Inorganic Nuclear Chemistry Letters* (5,337) authored by J. Servian and H. Buenafama which maintained that their neutron diffraction studies also confirmed the tetroxide lattice and the presence of Ag(III) and Ag(I) bonds in the lattice, a conclusion also reported previously by Naray-Szahn and Argay as a result of their x-ray diffraction studies (*Acta Cryst.* 1965, 19,180). Thus the effects of this invention can be explained in terms of these structural elucidations, namely, that the single molecular semiconductor crystal which inevitably must be electronically active exchanging two electrons per crystals between its mono and trivalent bonds is in reality a device which kills pathogens in the same manner as electrically active large-scale devices utilized in water supplies.

When the tetroxide crystals are utilized to destroy pathogens, they will not do so unless activated by an oxidizing agent. This is analogous to the behavior of single semiconducting photovoltaic molecular devices such as copper indium selenide whose surfaces must be "etched" in order to activate the photovoltaic activity, i.e., for light to facilitate the release of electrons from the molecule. The tetroxide was activated by persulfates. It was found that when the persulfates were tested as a control by themselves, they failed to exhibit any unilateral antipathogenic activity at the optimum level selected of 10 PPM. The persulfates evaluated varied from Oxone (Registered Trademark Du Pont Company) brand potassium monopersulfate to alkali peroxydisulfates.

DESCRIPTION OF THE DRAWING

In the drawing which illustrates the best mode presently contemplated for carrying out the present invention.

DESCRIPTION OF THE INVENTION

Figure 1:
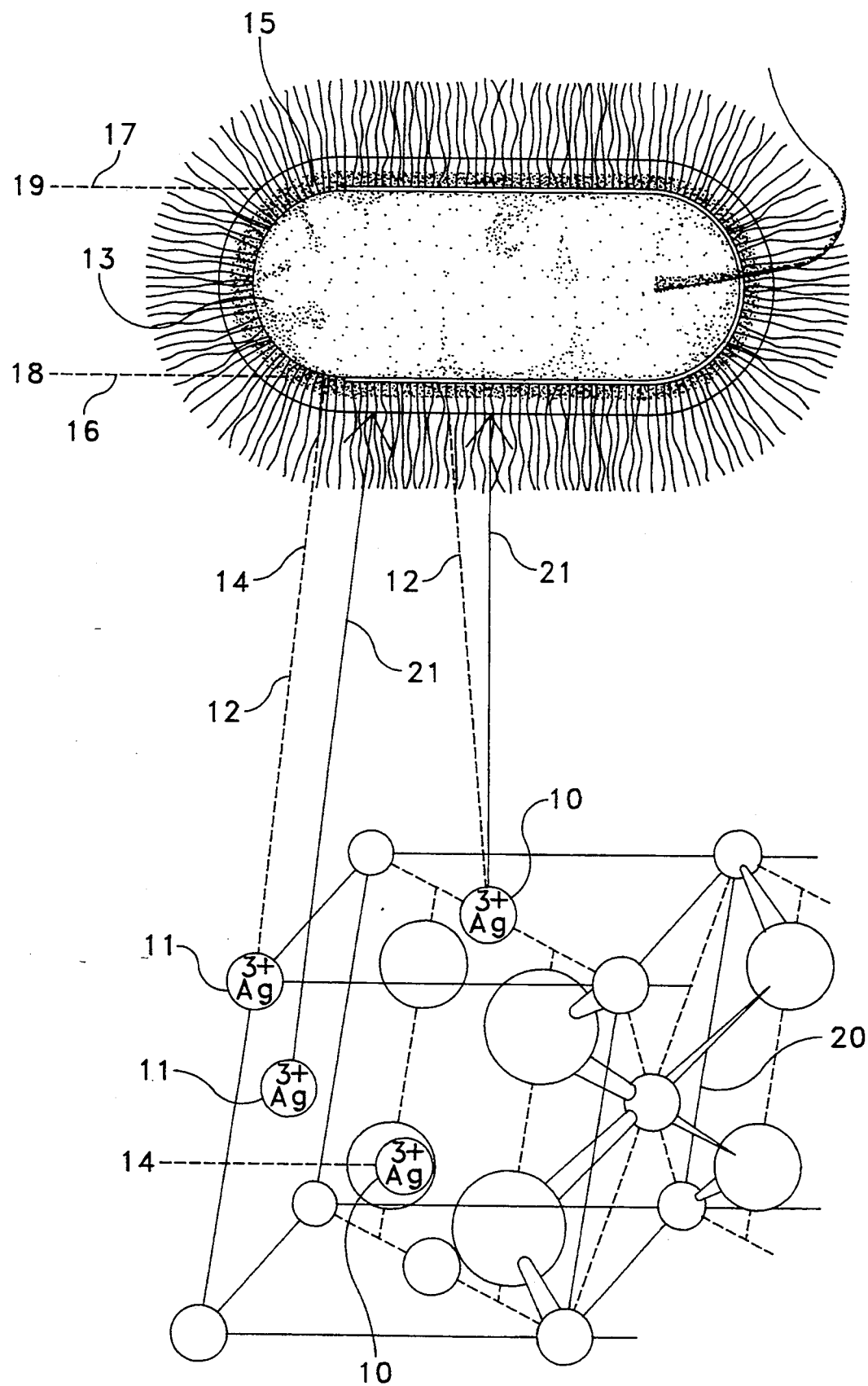
FIG. 1 is a diagrammatic view showing the crystal lattice of $Ag_4O_4$ attacking a pathogenic bacillus.

Turning now to Drawing FIG. 1 depicting the crystal lattice of $Ag_4O_4$, the device operates by transferring electrons from the monovalent silver ions 10 to the trivalent silver ions 11 in the crystal 20 through the aqueous media in which it is immersed and which conducts electrons depicted by the path 12, contributing to the death of pathogen 13 with electrons 14, traversing the cell membrane surface 15, said pathogen being "electrocuted" by not only these electrons but by others: 16 and 17 following paths 18, and 19 emanating from other molecular devices in the vicinity of the pathogen. The device is attracted to the cell membrane surface 15 by powerful covalent bonding forces 21 caused by the well-known affinity of silver to certain elements present in the membrane, such as sulfur and nitrogen. Drawing FIG. 1 exaggerates the size of the silver oxide molecular device with respect to that of a microorganism for depiction purposes only.

The electron transfer can be depicted by the following half reactions in which the monovalent silver ion loses an electron and the trivalent silver gains one as follows:

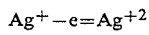

$$Ag^+ - e = Ag^{+2}$$

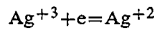

$$Ag^{+3} + e = Ag^{+2}$$

The molecular crystal then will become stabilized with each silver ion having a divalent charge.

Stringent testing was performed in which cultures were actually placed in trypticase soy nutrient broth, which allowed the pathogens being tested to replicate without being detached from its own food supply. Under these conditions the devices were able to kill two strains of E. Coli at 2.5 PPM; Micrococcus Luteus at 1.25 PPM; Staphylococcus aureus at 2.5 PPM; Staphylococcus epidermidis at 0.6 PPM; Pseudomonas aeruginosa at 1.25 PPM; and Streptococcus pyogenes at 2.5 PPM.

The devices were then evaluated in analogous nutrient used for yeasts, algae and molds utilizing Sabouraud dextrose broth. The infectious yeast pathogen Candida ALBICANS was totally killed at 2.5 PPM and that of the Saccharomycetpideae variety at 1.25 PPM.

If we are to consider one molecular device in operation, then each molecule would release two electrons having each a charge of $4.8 \times 10^{-10}$ e.s.u. equivalent to approximately $1.6 \times 10^{-19}$ coulombs. The EMF given in my *Encyclopedia of Chemical Electrode Potentials* (Plenum 1982), page 88, for the oxidation of Ag(I) to Ag(II) is 1.98 volts which approximates 2.0 V. The total power output per device can be calculated in watts by multiplying the power output for each electron by 2. Since power is the product of the potential times the charge, $P = EI$; for each electron it would be $$2.0 \times 1.6 \times 10^{-19} = 3.2 \times 10^{-19} \text{ watts}$$

From this, and using Avogadro's number, we can calculate that the power flux of one liter of solution containing 0.5 PPM of devices would be 0.064 watts. Since the electronic charges of the devices are directly proportional to the number of devices in solution, i.e., the concentration of the oxide in the solution, we can arbitrarily assign our own device power flux constant which can be used to gauge the concentrations of the devices required in order to kill particular organisms in specific environments. I have found the following formula useful for this purpose: Power Flux=EMF generated per molecule×Concentration×5 (the EMF being 4.0 volts per molecular device; and the concentration is in PPM). Utilizing this formula, the power flux to effectuate 100% kills for the following organisms is given in Table I which follows.

TABLE I

| Organism Name | Power Flux |
|---|---|
| *Escherichia coli* | 50.0 |
| *Staphylococcus aureus* | 50.0 |
| *Streptococcus faecalis* | 50.0 |
| *Streptococcus pyogenes* | 50.0 |
| *Candida albicans* | 50.0 |
| *Pseudomonas aeruginosa* | 25.0 |
| *Micrococcus luteus* | 25.0 |
| *Staphylococcus epidermidis* | 12.5 |

EXAMPLE 1

The molecular crystal devices were tested as to whether they could kill pathogenic microorganisms with the intent of utilizing them in pharmaceutical applications. Once it could be determined that the devices inhibited a particular microorganism, the minimal concentration required of the $Ag_4O_4$ molecular crystal devices was determined to inhibit the microorganism in nutrient broth. One family of pathogens that are known for their deleterious effects on humans are popularly called "staph" infections. These infections are commonly contracted in hospitals having lax infectious screening procedures. Accordingly, three staph strains were selected as follows for evaluation: Staphylococcus aureus 9027, 27543 and Staphylococcus epidermidis 12228. The inoculum nutrient broth was prepared according to AOAC specifications so as to contain 0.6–1 million organisms per drop of inoculum, each drop being equal to 0.05 ml. The broth itself was trypticase soy broth BBL 11766 prepared according to label instructions. Accordingly, the broth was prestandardized for the microorganisms in question in order to assure that the number of organisms remained constant within the margins of statistical allowance during the test period. Having carried out the procedures with 0.05 ml. of inoculum and having incubated the organisms for 24 hours at 34°-35° C., it was found that staph organism 9027 was inhibited at 2.5 PPM; number 27543 at 5.0 PPM; and the 12228 organism at 0.625 PPM all in the presence of 10 PPM sodium persulfate. This data was utilized to formulate a dermatological cream which would contain 100 PPM sodium persulfate and 10 PPM of device crystals to inhibit staph infections. The data was also utilized to formulate a surgical instrument sterilization formulation and a surgical scrub soap.

EXAMPLE 2

The procedures described in Example 1 were analogously followed for the yeast pathogen Candida ALBICANS using strain 16464 excepting that the nutrient broth was changed to accommodate this yeast pathogen to Sabouraud dextrose broth (Difco 038217-9). It was found that 2.5 PPM of molecular crystal devices completely inhibited the growth of this gynecological yeast infection. A gynecological cream and a douche were formulated against yeasts based on the results, as well as a cosmetic preservative.

EXAMPLE 3

The devices were tested against AIDS virus. The protocol used was that of the Ministry of Health of the State of Israel at their Virology Laboratory located at Tel HaShomer, Israel. AIDS viruses which had been grown in vitro in a tissue culture were isolated and exposed to the devices at device concentrations of 0.05, 1.0, 2.0, 3.0, 5.0 and 10.0 PPM. There was no evidence of AIDS suppression at all until the concentrations reached 5.0 and 10.0 PPM. At 5.0 PPM, 60% of the viruses were killed. AT 10.0 PPM, 75% of the viruses were killed. Extrapolation of this data reveals that at 18.0 PPM there would be total suppression of the virus. These test results indicate that the devices are capable of being used to destroy viruses in applications involving the proliferation and transmittal of the AIDS virus outside of, or for external application on, the human body as in cold sterilization, or the active component of chemical specialty lubricants used in condoms.

While there is shown and described herein certain specific examples embodying the invention, it will be manifest to those skilled in the art that various modifications and rearrangements of the invention may be made without departing from the spirit and scope of the underlying inventive concept and that the same is not limited to the particular forms herein shown and described except insofar as indicated by the scope of the appended claims.

What is claimed is:

1. A method of inhibiting the growth of pathogens in pharmaceutical and cosmetic products, said pathogens selected from the group consisting of E. coli, Micrococcus Luteus, Staphylococcus aureus, Staphylococcus epidermidis, Pseudomonas aeruginosa, Streptococcus pyogenes, Candida Albicans, and Saccharomycetpideae, which comprises introducing molecular semiconductor crystal devices of the molecule tetrasilver tetroxide ($Ag_4O_4$) in the presence of an oxidizing agent comprising a persulfate.

* * * * *